(12) United States Patent
Sudharsan

(10) Patent No.: US 10,745,368 B2
(45) Date of Patent: Aug. 18, 2020

(54) PURIFICATION OF PLASTICIZERS

(71) Applicant: Archer Daniels Midland Company, Decatur, IL (US)

(72) Inventor: Naveen Sudharsan, Malden, MA (US)

(73) Assignee: ARCHER DANIELS MIDLAND COMPANY, Decatur, IL (US)

( * ) Notice: Subject to any disclaimer, the term of this patent is extended or adjusted under 35 U.S.C. 154(b) by 384 days.

(21) Appl. No.: 15/540,458

(22) PCT Filed: Jan. 5, 2016

(86) PCT No.: PCT/US2016/012103
§ 371 (c)(1),
(2) Date: Jun. 28, 2017

(87) PCT Pub. No.: WO2016/114944
PCT Pub. Date: Jul. 21, 2016

(65) Prior Publication Data
US 2018/0002301 A1   Jan. 4, 2018

Related U.S. Application Data

(60) Provisional application No. 62/104,302, filed on Jan. 16, 2015.

(51) Int. Cl.
*C07D 301/32* (2006.01)
*B01D 17/04* (2006.01)
*B01D 17/00* (2006.01)
*C08K 5/00* (2006.01)
*C08K 5/1515* (2006.01)

(52) U.S. Cl.
CPC .......... *C07D 301/32* (2013.01); *B01D 17/00* (2013.01); *B01D 17/045* (2013.01); *C08K 5/0016* (2013.01); *C08K 5/1515* (2013.01)

(58) Field of Classification Search
CPC ........................... B01D 17/045; C08K 5/0016
USPC ................... 210/681, 684, 685, 687, DIG. 5
See application file for complete search history.

(56) References Cited

U.S. PATENT DOCUMENTS

2010/0249441 A1* 9/2010 Nonoguchi ............. C07C 67/03
554/124
2015/0337112 A1* 11/2015 Ghosh-Dastidar ... C08K 5/0016
524/311

* cited by examiner

*Primary Examiner* — Thuan D Dang
(74) *Attorney, Agent, or Firm* — William B. Miller

(57) ABSTRACT

Plasticizers are purified by contact with a coalescing filter to effect removal of ions, metals, monohydric alcohols, and polyhydric alcohols. The resulting purified plasticizer compositions are suitable for use in PVC due to their low levels of impurities that reduce PVC utility.

1 Claim, No Drawings

PURIFICATION OF PLASTICIZERS

CROSS-REFERENCE TO RELATED APPLICATIONS

This application is a national stage entry of International Application No. PCT/US2016/012103, filed Jan. 5, 2016, which claims benefit of United States Provisional Patent Application No. 62/104,302, filed Jan. 16, 2015, the entirety of each of which are incorporated by this reference.

BACKGROUND OF THE INVENTION

The present invention relates generally to processes for purification of plasticizer compositions. More specifically, the present invention relates to processes for purification of epoxidized ester plasticizers.

Such epoxidized fatty acid esters have lately been of considerable interest for use as renewable source-based or—derived plasticizers for various plasticized polymer compositions and end uses, including for alkyd resins, amino resins, epoxy resins (usually phenolic materials), phenolic resins, polystyrene, polyurethane, poly (vinyl alcohol) and unsaturated polyesters. In particular, such materials have been investigated for use in polyvinyl halide compositions.

Polyvinyl chloride (PVC), the most common vinyl halide polymer, finds commercial application in a rigid, substantially unplasticized form and in a plasticized PVC form. Rigid PVC, with which the present invention is not concerned, is used for pipework, ducts and the like in which high chemical resistance is needed but not flexibility or pliability. Plasticized PVC, on the other hand, finds application in films, sheeting, wire and cable coverings, moldings, conveyor belting, toys and hose, in addition to serving as a leather substitute and as a fabric covering for upholstered furniture, automotive seating and other articles.

Broadly speaking, plasticizers are materials which are combined with polymers such as polyvinyl chloride (hereinafter, PVC) to impart flexibility, extensibility and workability or some combination of these attributes to the polymer, as needed for a particular end use. In 1951, the International Union of Pure and Applied Chemistry (IUPAC) developed a universally accepted definition for a plasticizer as a substance or a material incorporated in a material (usually a plastic or an elastomer) to increase its flexibility, workability, or distensibility. Frequently, a combination of primary and secondary plasticizers is used, with the secondary plasticizers not acting in and of themselves to impart the desired attributes to the PVC but serving to improve the effectiveness of the primary plasticizer(s) and optionally offer other characteristics to a PVC composition in which the materials are incorporated.

Historically, the majority of primary PVC plasticizers have been petroleum-derived phthalates and benzoate compounds, dioctyl phthalate and diisononyl phthalate being notable examples. However, such petroleum-derived plasticizers are frequently expensive to produce and use because of fluctuations in the pricing and availability of petroleum, and are increasingly likely to remain so as petroleum reserves are reduced and new supplies prove more costly and difficult to secure. Further, certain of the petroleum-derived phthalate plasticizers have raised concerns for their potential to disrupt human endocrine activity, and regulatory controls have been established in a number of countries to address these concerns.

Unmodified renewable source derived oils, such as triacylglycerol oils, are largely incompatible with PVC resin, but certain modified derivatives of renewable source derived oils, such as epoxidized soybean oil (ESO), are compatible with PVC resin and have been actively investigated for use as a lower cost, renewable source derived alternative to the petroleum-based plasticizers, both as primary and secondary plasticizers. The interest in developing useful plasticizers from renewable sources, such as renewable source derived animal, algal, microbial, or plant (including vegetable) oils, has developed partly also from the expectation that such materials would be less likely to cause physiological disturbances or other injuries to persons coming into contact with products which require plasticizers in their composition. In recent years, as a result, a number of different renewable source-based plasticizers for PVC have been introduced in the literature and in the marketplace. The plasticizer compounds can be used alone or in various mixtures, including many other plasticizers known in the art, such as esters of dicarboxylic acids, citric acid, and the esters of aromatic dicarboxylic acids (e.g., phthalic acid esters). Particularly useful are mixtures comprising plasticizer compounds prepared from epoxidized triglycerides with a high degree of epoxidation for plasticizing PVC. Such epoxidized triglycerides can be typically exemplified by epoxidized soybean oil and epoxidized linseed oil, while other epoxidized renewable source derived oils are also useful. In such formulations, the epoxidized fatty acid fragments provide a desired stabilizing effect by acting as scavengers of acidic polymer decomposition products. The plasticizer compounds are useful to make various industrial and consumer articles, including flooring materials, siding elements for exteriors and interiors of buildings, window frames, flexible and rigid pipes, tubing, reinforced hoses, artificial leather, packaging of consumer articles, interior and exterior automotive parts, electronic equipment cases, various single and multi-layered films, vinyl office supplies, plastisols, and the like.

The purified epoxidized ester plasticizers of the present invention can be made by either transesterification or interesterification and a purification process according to the present invention, for use subsequently as primary or secondary plasticizers in a variety of polymers, including halogenated polymers, acid-functionalized polymers, anhydride-functionalized polymers, and nitrile rubbers. An exemplary halogenated polymer is a PVC polymer, where "PVC" or "polyvinyl chloride" as used herein is understood to cover the range of homo—and copolymers of vinyl chloride with typically up to 20% of co-monomers such as vinyl acetate, propylene, ethylene, diethyl maleate, dimethyl fumarate and other ethylenically unsaturated co-monomers. Examples of other halogenated polymers include polyvinyl halide polymers, chlorinated polyolefins and chlorinated rubbers. Suitable acid-functionalized polymers include acrylic acid-functionalized polymers, as well as acrylic and other polymers in need of plasticization to reduce glass transitions or improve toughness.

Where used as primary plasticizers, the purified epoxidized fatty acid esters can comprise preferably at least 20 percent by weight of a polymer composition, more preferably will comprise at least 30 percent by weight of a polymer composition, and most preferably will comprise at least 50 percent by weight of a polymer composition. A suitable composition can comprise a plastisol.

The resultant plasticized polymer compositions can be formulated, it is noted, in all other respects in a conventional manner, including with incorporating various kinds of additives in addition to the inventive purified epoxidized esters. When the purified epoxidized esters are used in preferred embodiments as the primary plasticizers of a primary/secondary plasticizer system, for example, a renewably-based secondary plasticizer and thermal stabilizer such as epoxidized soybean oil can be added, or other secondary plasticizers (including petroleum-based plasticizers) or other additives for improving one or more properties of heat stability, lubricity or weathering resistance, as ultraviolet absorbers, fillers, anti-oxidants, anti-static agents, anti-fogging agents, pigments, dyestuffs, crosslinking aids and the like can be incorporated in the compositions. The inventive purified epoxidized esters may also be used in certain embodiments in combination with other primary plasticizers such as dioctylphthalate, other phthalates, citrates, benzoates, trimellitates, and other aliphatic diesters, though preferably the plasticized polymer compositions of the present invention will not include any added phthalates and will include substantially only renewably-based or biobased plasticizers.

The epoxidized ester plasticizers to be purified according to the present invention are synthesized by known routes. For example, in commonly-assigned, co-pending U.S. patent application Ser. No. 14/125,602, published Apr. 24, 2014 as US Pat. Appl. Pub. No. 2014/0113999 for "Reduced Color Epoxidized Esters from Epoxidized Natural Fats and Oils", the contents of which are hereby incorporated by reference in their entirety, reduced color epoxidized fatty acid esters (such as epoxidized methyl soyate, EMS) are made from an epoxidized natural fat or oil (such as epoxidized soybean oil, ESO) through the inclusion of borohydride in either a transesterification process or in an interesterification process.

In another example, in commonly-assigned, co-pending U.S. patent application Ser. No. 14/350,590, published Sep. 4, 2014 as US Pat. Appl. Pub. No. US 2014/0249322 for "Making Epoxidized Esters from Epoxidized Natural Fats and Oils", the contents of which are hereby incorporated by reference in their entirety, epoxidized esters are made by a transesterification process using low moisture fats and oils. The products undergo phase separation, and reduced molar excesses of alcohol may be employed compared to processes not employing a low moisture feedstock.

In another example, in commonly-assigned U.S. Pat. No. 8,703,849, "Processes for Making High-Purity Renewable Source-Based Plasticizers and Products Made Therefrom", issued Apr. 22, 2014, the contents of which are hereby incorporated by reference in their entirety, we described processes for making certain high purity unsaturated fatty acid esters from alcohols including 5 to 7 members in a ring structure, whether cyclic, heterocyclic or aromatic in character, which esters could then be epoxidized (according to a second aspect) to yield renewable source-based plasticizers for polyvinyl halide polymers, and in particular, for PVC. The plasticizers could be incorporated easily into PVC as primary plasticizers at even plastisol levels, and provided plasticized PVC compositions in turn that exhibited improved and unexpected performance in certain respects.

While epoxidized benzyl esters of unsaturated fatty acids had been described or suggested previously for plasticizing PVC, see for example, U.S. Pat. No. 3,377,304 (epoxidized benzyl soyate) and British patent No. GB 1,049,100, the known methods of making those benzyl esters and subsequent plasticizers resulted in PVC compositional limitations and performance characteristics which had unfortunately limited the use of such materials only to be secondary plasticizers and thermal stabilizers.

We found that by preparing the indicated unsaturated fatty acid esters (including, of course, benzyl soyate esters), whether by reacting alcohols including 5 to 7 members in a ring structure with unsaturated fatty acid lower alkyl esters having low residual monoglycerides and diglycerides or by reacting the alcohols with an unsaturated fatty acid feed having a correspondingly low monoacylglycerol and diacylglycerol content, these limitations could be overcome.

One very important attribute of plasticizers is the degree of purity of the plasticizer. After plasticizer synthesis, common impurities include metals, ions, monohydric alcohols, such as methanol or benzyl alcohol, and polyhydric alcohols, such as glycerol. Impurities in plasticizers present several problems in the plasticizer and products made therefrom. Impurities may impart odors or colors to plasticizers. Metals and ions are especially problematic plasticizer impurities; they can interfere with the electrical properties of plastics that they are incorporated into, such as their electrical insulating ability. Nonhomogeneity of the polymer crystallite interstices is a result of contaminating ions in plasticized PVC: "The ions move through free spaces which exist in the non-crystalline part between polymer crystallites. The free spaces have nonhomogeneous size distribution depending on a property of polymers or crystallization conditions. The homogeneity or nonhomogeneity of the size of the free space affects the ionic motion, and consequently it also affects the electrical properties of polymer solids." ("*Study of motion of impurity ions making influence on electrical properties of polymer solids in low frequency range,*" Anada, Y., Advanced Materials Research, 740, 630-635, 2013 (Trans Tech Publications Ltd.)). In PVC plastisols, the electrochemical potential (zeta potential) of PVC particles is related to plasticizer exudation. ("*An attempt to describe nonspecific interactions of polymer-polymer type in the plastisol dispersions of poly(vinyl chloride),*" Makarewicz, E., Colloid and Polymer Science 267(9), 803-7, 1989). The zeta potential of PVC particles is in turn influenced by the ionic impurities contained in the particles, which originated from additives. This can be very important in the final product, because the presence of even small amounts of acid or alcohol impurities in plasticizers can reduce the efficiency of the plasticizer. (http://www.plastemart.com/Plastic-Technical-Article.asp?LiteratureID=1602&Paper=essential-compounding-chemicals-used-with-PVC-resin-primary-secondary-plasticiser-heat-light-stabilisers, accessed Jul. 3, 2014).

Another potential source of impurities in epoxidized ester plasticizers is the characteristic oxirane ring. The labile nature of the epoxide functionality in the epoxidized renewable source derived fats or oils contemplated as starting materials for epoxidized esters renders the epoxides susceptible to formation of undesired by-products. This highly reactive ring is easily opened, and shows the typical reactions of ethylene oxide. Oxirane ring compounds are highly sensitive to acid-catalyzed reactions. They are also susceptible to reacting with alcohols, amines, carboxyl groups, imines, phenols, and inorganic cyanates. ("*Epoxidation Products of Fatty Acids, Alkyl Fatty Acid Esters and Glycerides, etc. as Chemical Intermediates and Plasticizer/Stabilizers for Polymers, Resins and Rubbers, Part I*" Lower, E. S., SOFW Journal 121(4) 278, 280-2 1995).

The problem of by-products arising from hydrolysis or rearrangement of epoxides and from cross-linking of the fatty acid chains is a recognized source of impurities in epoxidized ester plasticizers (U.S. Pat. No. 8,436,042, issued May 7, 2013, the contents of which are hereby incorporated by reference in their entirety).

Therefore, considerable effort is often expended to remove impurities from plasticizers due to the disproportionate negative effect of impurities on the properties of compositions, including PVC plastics, they are incorporated into. Unfortunately, the known approaches to plasticizer purification are cumbersome and costly. Plasticizers are often slightly acidic due to the presence of small amounts of organic acids. Acids in plasticizers, even at low concentrations, attack the plasticizer and will cause discoloration of PVC on exposure to slight heating. Washing (extraction with water) is often carried out on an industrial scale in the reactor vessel used to synthesize a plasticizer. The washing process is expensive, and consumes valuable reactor time that could be used in plasticizer production. Ironically, the water washing also generates large amounts of waste wash water, thus reducing process sustainability by running counter to the very values promoted by the use of renewable source derived plasticizers.

Metal ions and their corresponding salts are notoriously problematic in PVC for causing degradation, including photodegradation, of the PVC. Metal salt contaminants increase the light-sensitivity of PVC by acting as sensitizers of the decomposition of peroxide groups or by generating free radicals under UV irradiation. Typical ionic and metal contaminants in plasticizers include sodium, iron, calcium, phosphorus, zinc, boron, molybdenum, and aluminum.

One example of plasticizer purification is taught in U.S. Pat. No. 3,070,608 (issued Dec. 25, 1962, assigned to Swift & Company), which required extraction of methyl esters of epoxy acids with "a large volume of water" (Example 1, Col 3 line 4); the washing removed "excess alcohol, glycerine, and sodium methylate catalyst" (Example 4, Col 4 lines 20-23. Subsequent drying was also necessary. The use of a large volume of water is believed to be cumbersome and costly.

Another example of plasticizer purification is taught in U.S. Pat. No. 8,802,877 (issued Aug. 12, 2014; assigned to NPC Industrias Quimicas Ltda). In this application, product mixture purification required several steps:

"At the end of the transesterification reaction a purification step occurs through which the formed glycerin is decanted and separated. The reaction mixture is then neutralized with acid, washed and stripped (alcohol removal process), with steam and under a discreet vacuum (up to about 600 mmHg [80 kPa]), at temperatures varying from 120 to 220° C., depending on the type of alcohol which is retrieved and re-used in subsequent production. After the alcohol removal process, the product is filtered." (Col. 7 lines 4-12)

The high-temperature stripping with steam can cause formation of heat-related defects, such as color defects, and the execution of so many steps is believed to be cumbersome and costly.

Yet another example of plasticizer purification is set forth in European Patent Application Publication No. EP2 070 980 (published Jun. 17, 2009, assigned to Nexoleum Bioderivados Ltda.). After the formation of epoxidized ethyl soyate plasticizer, phase separation was carried out in a separation funnel as follows:

"At the end of the reaction, the water phase is separated from the oil phase in a separation funnel. The oil phase contains the epoxidized ester and the formic acid. The wash of the oil phase is processed according to the procedure described for the wash of the ethyl ester after the transesterification; although the water needs to be preheated to 50° C. and the wash procedure shall be repeated until all the formic acid has been eliminated." Page 3 lines 47-51

The execution of repeated washings with water preheated to 50° C. is believed to be cumbersome and costly.

Another example of plasticizer purification is taught in United States Patent Application Publication No. US2013/203907 (published Aug. 8, 2013, assigned to Arkema, Inc.). Residual sodium, calcium and/or magnesium ions, contaminants, and detrimental reaction by-products were removed from epoxidized plasticizers with one or two water-washing steps to remove hydrogen peroxide and formic acid. The compositions are then subjected to steam-stripping and drying under full vacuum (Example 1, [0043] of US2013/203907). The high-temperature stripping with steam can cause formation of heat-related defects, such as color defects.

In commonly-assigned United States Patent Application Publication No. US2014/113999, epoxidized methyl soyate having a Pt—Co Hazen color of 90 or less as determined by ASTM D1209 was obtained after neutralization with a solution of citric acid, three or four iterative water washes, drying over anhydrous magnesium sulfate, filtration, and vacuum drying overnight.

In another example of plasticizer purification, double distillation is proposed to remediate odor problems in plasticizers at (http://www.plastemart.com/Plastic-Technical-Article.asp?LiteratureID=1602&Paper=essential-compounding-ehemicals-used-with-PVC-resin-primary-secondary-plasticiser-heat-light-stabilisers, accessed Jul. 3, 2014). However, subjecting the plasticizer to double distillation can cause the formation of heat-related defects, such as color defects.

The present invention in one aspect addresses this need, in providing a process for purifying epoxidized ester plasticizer compositions. The process is simple and continuous, and does not require the high temperatures used in distillation.

SUMMARY OF THE INVENTION

The present invention concerns the discovery that the removal of ions and other impurities from renewable source derived plasticizers can be carried out without any of the disadvantages indicated above. More particularly, according to the process of the present invention generally, a plasticizer is purified by coalescence. In the inventive method, plasticizers can be purified without the cumbersome and expensive approaches of the prior art. Purification of the plasticizer compositions can be carried out without exposure to heat, vacuum, extraction/washing steps, intense agitation, lengthy phase separation times, or steam.

DETAILED DESCRIPTION OF THE INVENTION

Epoxidized methyl soyate (CAS No. 68082-35-9) is an example of a suitable plasticizer for purification by the methods of the present invention.

Other suitable candidates for use in the present invention include plasticizers derived from epoxidized esters, such as levulinate ester plasticizers and angelicalactone plasticizers as set forth in U.S. Pat. No. 8,436,042, issued May 7, 2013, the contents of which are hereby incorporated by reference in their entirety; vegetable oil derived plasticizers as disclosed in U.S. Pat. No. 6,797,753, issued Sep. 28, 2004 the contents of which are hereby incorporated by reference in their entirety; the primary and secondary plasticizers disclosed in U.S. Pat. No. 8,557,139, issued Aug. 20, 2009, the contents of which are hereby incorporated by reference in their entirety; unhindered polyol plasticizers as disclosed in U.S. Pat. No. 8,383,708, issued Feb. 23, 2013, the contents of which are hereby incorporated by reference in their entirety; partially transesterified epoxidized bioesters as disclosed in U.S. Pat. No. 8,623,947, issued Jan. 7, 2014, the contents of which are hereby incorporated by reference in their entirety; and, plasticizers for use in non-PVC plastics, such as plasticizers for the polylactic acid-based polymeric material disclosed in U.S. Pat. No. 6,869,985 (issued Mar. 22, 2005), U.S. Pat. No. 7,256,223 (issued Aug. 14, 2007), and U.S. Pat. No. 7,354,656 (issued Apr. 8, 2008), the contents of all of which are hereby incorporated by reference in their entirety. The solution can also be applied to other PVC plasticizers, including phthalates, allyl phosphate esters, dialkylether diesters, tricarboxylic esters, epoxidized oils, epoxidized esters, polyesters, polyglycol diesters, alkyl, allyl ether diesters, aliphatic diesters, alkylether monoesters, citrate esters, dicarboxylic esters, vegetable oils, glycerine esters, FDCA esters, isohexide esters, and other plasticizers used in conventional polyvinyl chloride applications, or any plasticizer produced by a process that produces metals or ionic side products or uses a water neutralizing step as well.

The term "epoxidized natural oil," as used herein, is a natural oil wherein at least one fatty acid moiety contains at least one epoxide group. Epoxidation of unsaturated fatty acid esters from renewable source derived oils, even in the form of a methyl ester such as methyl soyate, typically generates an epoxy group, also called a glycidyl group or oxirane ring, replacing a double bond in the fatty acid backbone. Non-limiting examples of suitable epoxidized renewable source derived oils include epoxidized algae oil, epoxidized microbial oil, epoxidized animal fats, such as epoxidized beef tallow oil and epoxidized fish oil, epoxidized plant oils, epoxidized canola oil, epoxidized castor oil, epoxidized corn oil, epoxidized linseed oil, epoxidized palm oil, epoxidized rapeseed oil, epoxidized safflower oil, epoxidized soybean oil, epoxidized sunflower oil, epoxidized tall oil, epoxidized tung oil, and any combination thereof.

The epoxidized renewable source derived fat or oil can be derived from renewable source derived animal, algal, microbial, or plant (including vegetable) sources. Preferably the epoxidized renewable source derived fat or oil is a vegetable or seed oil, for example, soybean oil, linseed oil, corn oil, sunflower oil, canola oil, rapeseed oil, coconut oil, palm kernel oil, palm oil, cottonseed oil, peanut oil, olive oil, tall oil, safflower oil, genetically modified oil, and derivatives and mixtures thereof. Preferably, the oil is a polyunsaturated oil selected from the group above. Most preferably, the polyunsaturated oil is low in C18:3 or higher fatty acids. Although any polyunsaturated oil that has sufficiently low levels of C18:3 or higher fatty acids is suitable for the present method, preferably, the oil is safflower oil, sunflower oil or corn oil. Preferred oils contain less than about 2 percent of C18:3 or higher polyunsaturated fatty acids. More preferably, the oils contain less than about 1 percent of C18:3 or higher polyunsaturated fatty acids. Also preferred are polyunsaturated oils containing less than about 2 percent linolenic acid. More preferably, the linolenic content is less than about 1 percent. Suitable examples of renewable source derived epoxidized esters include epoxidized methyl soyate and epoxidized benzyl soyate. It is understood that "soyate" is a carboxylate moiety which refers to any naturally occurring or subsequently refined mixture of fatty acids and their esters, where the fatty acids include palmitic acid, stearic acid, oleic acid, linoleic acid, linolenic acid, and the like.

The epoxidized renewable source derived plasticizers can be purified using a coalescer. The coalescer allows for continuous room temperature flow to remove metals, ions and alcohol impurities from plasticizers without exposing the plasticizer to heat, vacuum, extraction/washing steps, intense agitation, lengthy phase separation times, or steam. The purified plasticizer leaves the coalescer as a purified effluent, and the impurities are removed through another exit port.

Impurities that the present invention contemplates removing from epoxidized ester plasticizer compositions include ions, metals, monohydric alcohols, and polyhydric alcohols.

Typical ionic and metal contaminants in plasticizers include sodium, iron, calcium, phosphorus, zinc, boron, molybdenum, and aluminum.

Monohydric alcohols are linear or branched primary or secondary monoalkanols or alkoxyalkanols having from 1 to 12 carbon atoms. The characteristic feature of monohydric alcohols is the presence of a single free hydroxyl group. Examples of alkanols are methanol, ethanol, n-propanol, isopropanol, n-butanol, secondary butanol, allyl alcohol, isobutanol, isoamyl alcohol, benzyl, n-pentanol, iso-pentanol 2-ethylhexanol. The monohydroxyl alcohols can be primary, secondary or tertiary alcohols of annular, straight or branched chain compounds. Alkoxyalkanols are primary or secondary alcohols having from 3 to 12 carbon atoms, wherein a linear, branched, or cyclic alkoxy group having from 1 to 8 carbon atoms is located at a vicinal position to the hydroxyl group and include methoxypropanol, ethoxypropanol, propoxypropanol, isopropoxypropanol, and 3-methoxy-2-methylpropanol. Such alkoxyalkanols are typically derived by opening an alkyl oxirane with an alkanol. Another suitable example of an alkoxyalkanol is tetrahydrofurfuryl alcohol readily accessible via hydrogenation of furfural.

Polyhydric alcohols are linear or branched polyhydroxylated alkanes having 2 or more free hydroxyl groups. Typical examples are ethylene glycol, propylene 1,2- and 1,3-diols, butylene glycol isomers, glycerol, 1,2,4-trihydroxybutane, pentaerythritol, xylitol, ribitol, sorbitol, mannitol, and galactitol. Polyhydric alcohols can optionally contain one or more ether bonds, and suitable examples of such polyhydric alcohols are isohexitols such as isosorbide, sorbitan isomers, diglycerol, and polyglycerols.

In an embodiment of the present invention, the present invention comprises a process for purifying plasticizer compositions, comprising contacting a plasticizer composition containing at least one impurity selected from the group consisting of ions, metals, monohydric alcohols, and polyhydric alcohols with a coalescing filter to effect phase separation into a phase enriched in impurities and a purified plasticizer effluent phase; wherein the content of at least one impurity is reduced in the purified plasticizer effluent phase. In another embodiment, a composition comprising at least one plasticizer composition purified according to the process is obtained.

In another embodiment, the present invention further comprises recovering the purified plasticizer effluent phase.

In yet another embodiment, the purified plasticizer effluent phase is characterized by a content of 40 ppm or less of at least one metal or ion selected from the group consisting of sodium, iron, calcium, phosphorus, zinc, boron, molybdenum, and aluminum. In another embodiment, the purified plasticizer effluent phase is characterized by an ion content of 10 ppm or less of at least one metal or ion selected from the group consisting of sodium, iron, calcium, phosphorus, zinc, boron, molybdenum, and aluminum. In yet another embodiment, the purified plasticizer effluent phase is characterized by the reduction of at least one metal or ion content to below the detection limits of an ICP spectrometer, wherein the metal or ion content of the plasticizer was above the detection limits of the ICP spectrometer before contacting with the coalescing filter.

In another embodiment, the purified plasticizer effluent phase is characterized by a reduction in content of at least one monohydric alcohol. In still another embodiment, the purified plasticizer effluent phase is characterized by a reduction in a sum of contents of two or more monohydric alcohols, wherein the reduction in the sum of contents of monohydric alcohol is 30% or more. In another embodiment, the purified plasticizer effluent phase is characterized by a reduction in a sum of contents of two or more monohydric alcohols, wherein the reduction in the sum of contents of monohydric alcohol is 60% or more.

In yet another embodiment, the purified plasticizer effluent phase is characterized by a sum of contents of monohydric alcohol of less than 0.5%

In another embodiment, the monohydric alcohol comprises at least one member selected from the group consisting of methanol, ethanol, n-propanol, isopropanol, n-butanol, secondary butanol, allyl alcohol, isobutanol, isoamyl alcohol, n-pentanol, iso-pentanol 2-ethylhexanol, alkoxyalkanols, methoxypropanol, ethoxypropanol, propoxypropanol, isopropoxypropanol, 3-methoxy-2-methylpropanol, benzyl, and tetrahydrofurfuryl alcohol.

In yet another embodiment, the purified plasticizer effluent phase is characterized by a reduction in a sum of contents of polyhydric alcohols. In another embodiment, the reduction in the sum of contents of polyhydric alcohols is 20% or more. In a still further embodiment, the reduction in the sum of contents of polyhydric alcohol is 40% or more.

In an embodiment, the purified plasticizer effluent phase is characterized by a sum of contents of polyhydric alcohol less than 0.25%.

In another embodiment, the polyhydric alcohol comprises at least one member selected from the group consisting of linear or branched polyhydroxylated alkanes having 2 or more free hydroxyl groups, ethylene glycol, propylene 1,2-diol, propylene 1,3-diol, butylene glycol, glycerol, 1,2,4-trihydroxybutane, pentaerythritol, xylitol, ribitol, sorbitol, mannitol, galactitol, isohexitol, isosorbide, sorbitan, diglycerol, and polyglycerol.

In yet another embodiment, contacting the plasticizer composition containing at least one impurity with a coalescing filter to effect phase separation is carried out without additional heating. In an embodiment, contacting the plasticizer composition containing at least one impurity with a coalescing filter to effect phase separation is carried out at ambient temperature. In another embodiment, the present invention comprises a composition comprising at least one purified plasticizer effluent phase purified according to the processes recited herein.

In yet another embodiment, the present invention comprises a process for purifying epoxidized ester plasticizer compositions, comprising contacting an epoxidized ester plasticizer composition containing at least one impurity selected from the group consisting of ions, metals, monohydric alcohol, and polyhydric alcohol with a coalescing filter to effect phase separation into a phase enriched in impurities and a purified epoxidized ester plasticizer effluent phase, wherein the content of at least one impurity is reduced in the purified epoxidized ester plasticizer effluent phase.

The present invention is further demonstrated by the examples that follow:

Example 1

Synthesis of Epoxidized Methyl Soyate

Epoxidized methyl soyate was synthesized substantially as described in the aforementioned co-pending United States Patent Application Publication No. US2014/249322. One thousand grams of epoxidized soybean oil was dried by means of a rotary evaporator for 1 hour in a 90 degrees Celsius water bath. The dried ESO was added to a jacketed glass reactor along with 275 grams anhydrous methanol. The mixture was stirred at 55 degrees Celsius as a mixture of 1 gram sodium borohydride dissolved in a sodium methoxide (3 grams)/methanol (25 grams) solution was added. The reaction continued at 55 degrees with stirring for about 60 minutes, at which point a solution of about 10 grams of citric acid in 30 mL of methanol was added. Excess methanol was removed under vacuum in the rotary evaporator.

Preparation for Coalescing

The reactor contents were then moved to a separatory funnel and allowed to phase-separate. The lower, glycerol-containing layer was removed and the top layer was washed once with 300 milliliters of deionized water. After phase separation, the lower aqueous layer was removed, and the top epoxidized ester reaction product layer was dried under vacuum on a rotary evaporator. The epoxidized ester reaction product was visibly turbid/cloudy. The interfacial tension (IFT) between the epoxidized ester product (epoxidized methyl soyate, EMS) and glycerol was determined; the IFT value was to be 8.5 dynes/cm.

Purification of Epoxidized Methyl Soyate

The epoxidized ester reaction product was contacted with a PhaseSep™ Y separation cartridge (Pall Corporation, Port Washington, N.Y.) by passing the epoxidized ester reaction product through a liquid/liquid coalescer filter apparatus at 100 mL/minute at room (ambient) temperature.

Phase separation was effected to yield two phases: 1) a phase enriched in impurities, and 2) a phase comprising purified epoxidized ester plasticizer. The separated phases were collected. The purified epoxidized ester plasticizer phase was clear and completely free of the visible turbidity/cloudiness of the unpurified epoxidized ester reaction product. Ions and metals in the purified epoxidized ester plasticizer phase were quantified using a Spectro Arcos ICP spectrometer (Kleve, Germany). The composition of the untreated epoxidized ester reaction product and the purified epoxidized ester plasticizer after passing through the coalescing filter is given in Table 1. All ion and metal units are mg/kg (PPM).

| Ion/metal Impurity | Epoxidized ester reaction product | Purified epoxidized ester plasticizer | Impurity reduction |
| --- | --- | --- | --- |
| Na | 46.0 | ND | complete |
| Fe | 97.7 | ND | complete |
| Ca | 17.8 | 5.24 | 70% |
| P | 8.73 | ND | complete |
| Zn | 6.39 | ND | complete |
| B | 2.52 | ND | complete |
| Mo | 1.58 | ND | complete |
| Al | 0.391 | ND | complete |
| Total ions and | 181.08 | 5.24 | 97% |

-continued

| Ion/metal Impurity | Epoxidized ester reaction product | Purified epoxidized ester plasticizer | Impurity reduction |
|---|---|---|---|
| metals (PPM) | | | |
| Methanol (wt %) | 1.24 | 0.48 | 61% |
| Glycerol (wt %) | 0.38 | 0.2 | 47% |

The purified epoxidized ester plasticizer was significantly less turbid than the untreated epoxidized ester reaction product. Surprisingly, the content of ions and metals in the purified epoxidized methyl soyate plasticizer (coalescer effluent) contained only 5.24 parts per million of calcium and was completely purified from the other ion and metal contaminants in the feed (the detection limits of the method were 0.05 ppb for P and Mo and 0.01 ppb for the remaining ions and metals). The purified epoxidized methyl soyate plasticizer was significantly reduced in metal/ion impurities (97% reduction), in monohydric alcohol (methanol, 61%), polyhydric alcohol (glycerol, 47%).

Example 2

Epoxidized methyl soyate was synthesized substantially as described in Example 1 except that the EMS reaction product was rotovapped to remover methanol, then fed directly to the coalescer without the "preparation for coalescing" steps of phase separation, removal of the lower aqueous layer, and drying of the top epoxidized ester reaction product layer to emulate a continuous process without these steps. After rotary evaporation the residue split into two phases. The distribution of glycerol, methanol, sodium, and boron between the phases and the distillate are shown in Table 2.1.

TABLE 2.1

Distribution of components between the phases and distillate.

| Phase | Glycerol | Methanol | Sodium | Boron |
|---|---|---|---|---|
| Tops | 6.5% | 1.4% | 4.7% | 40.7% |
| Bottoms | 93.5% | 0.2% | 95.3% | 59.3% |
| Distillate | 0.0% | 98.5% | 0.0% | 0.0% |

To emulate a continuous process without the phase separation, the two phases were combined to form a cloudy suspension. The suspension was passed through a two inch/5 cm section of PhaseSep® A/S Series Liquid/Liquid Coalescer Element LCS5FPS200966 in a stainless steel bench-scale coalescer built to accommodate a 2 inch/5 cm coalescing filter element. This coalescing element is similar to the PhaseSep Y previously used, but is designed for the biodiesel industry. The cloudy top phase was passed through the coalescer at 20 mL/minute without formation of two phases. A clear single phase was collected due to the retention of glycerol on the membrane, which does not simulate a continuous process.

To simulate a continuous process, the 5 cm (2") membrane was saturated with glycerol by passing the glycerol-rich bottom phase through the membrane. The remaining bottom phase, the top phase, and the methanol was mixed together and evaporated to remove methanol. The residue formed two phases and the cloudy top phase was passed through the coalescing membrane, resulting in formation of two phases. After 30 minutes, the top phase was tested. The levels of glycerol, sodium and boron were substantially unchanged, but the level of methanol was reduced by greater than 50% (51.5%) with this type of coalescing membrane (Table 2.2).

TABLE 2.2

Levels of methanol, glycerol, sodium and boron before and after contacting with a PhaseSep ® A/S Series Liquid/Liquid Coalescer Element LCS5FPS200966.

| Description | Methanol mg/kg | Glycerol % w/w | Na mg/kg | B mg/kg |
|---|---|---|---|---|
| Before | 4603 | 0.299 | 11.1 | 2.0 |
| After | 2237 | 0.269 | 13.6 | 3.6 |

Example 3

Synthesis of Epoxidized Benzyl Soyate

In a prophetic example, epoxidized benzyl soyate is prepared substantially as described in Example 1, except benzyl alcohol is substituted for methyl alcohol. The product is allowed to cool under vacuum to room temperature and neutralized with a citric acid solution to yield epoxidized benzyl soyate product mixture containing a significant volume of benzyl alcohol.

Purification of Epoxidized Benzyl Soyate

Epoxidized benzyl soyate product mixture containing benzyl alcohol is contacted with a coalescing filter unit substantially as outlined in Example 1 and a purified epoxidized ester plasticizer phase (epoxidized benzyl soyate, EBS) is collected. The content of metals and ions, benzyl alcohol and glycerol in the purified epoxidized ester plasticizer EBS phase is lower than the untreated epoxidized benzyl soyate reaction product. The coalescer effluent is substantially less turbid than the untreated epoxidized benzyl soyate reaction product.

Example 4

Synthesis of Epoxidized Ethyl Soyate

In a prophetic example, epoxidized ethyl soyate is prepared substantially as described in Example 1, except ethyl alcohol is substituted for methyl alcohol. The product is allowed to cool under vacuum to room temperature and neutralized with a citric acid solution to yield epoxidized ethyl soyate product mixture containing a significant volume of ethyl alcohol.

Purification of Epoxidized Ethyl Soyate

Epoxidized ethyl soyate product mixture containing ethyl alcohol is contacted with a coalescing filter unit substantially as outlined in Example 1 and a purified epoxidized ester plasticizer phase (epoxidized ethyl soyate, EES) is collected. The content of metals and ions, ethyl alcohol and glycerol in the purified epoxidized ester plasticizer EBS phase is lower than the untreated epoxidized ethyl soyate reaction product. The purified epoxidized ester plasticizer phase is substantially less turbid than the untreated epoxidized ethyl soyate reaction product.

Example 5

Synthesis of Epoxidized Isoamyl Soyate

In a prophetic example, epoxidized isoamyl soyate is prepared substantially as described in Example 1, except isoamyl alcohol is substituted for methyl alcohol. The product is allowed to cool under vacuum to room temperature and neutralized with a citric acid solution to yield epoxidized isoamyl soyate product mixture containing a significant volume of isoamyl alcohol.

Purification of Epoxidized Isoamyl Soyate

Epoxidized isoamyl soyate product mixture containing isoamyl alcohol is contacted with a coalescing filter unit substantially as outlined in Example 1 and a purified epoxidized ester plasticizer phase (epoxidized isoamyl soyate, EIS) is collected. The content of metals and ions, isoamyl alcohol and glycerol in the purified epoxidized ester plasticizer EBS phase is lower than the untreated epoxidized isoamyl soyate reaction product. The purified epoxidized ester plasticizer phase is substantially less turbid than the untreated epoxidized isoamyl soyate reaction product.

What is claimed is:

1. A process for purifying epoxidized ester plasticizer compositions, comprising;
    contacting an epoxidized ester plasticizer composition containing one or more of sodium, iron, calcium, phosphorus, zinc, boron, molybdenum and aluminum ions/metals, monohydric alcohol, and polyhydric alcohols with a coalescing filter to effect separation into a phase enriched in at least one of these ions, metals, monohydric or polyhydric alcohols compared to a purified effluent containing a lesser amount of the ion or ions, metals, monohydric or polyhydric alcohols in which the other phase is enriched.

* * * * *